United States Patent [19]
Kalz et al.

[11] Patent Number: 6,121,452
[45] Date of Patent: Sep. 19, 2000

[54] PROCESS FOR THE PREPARATION OF QUINOPHTHALONES

[75] Inventors: Dietmar Kalz, Neunkirchen; Stephan Michaelis, Odenthal; Karl-Heinz Reinhardt, Monheim, all of Germany

[73] Assignee: Bayer Aktiengesellschaft, Leverkusen, Germany

[21] Appl. No.: 08/921,764

[22] Filed: Aug. 28, 1997

[30] Foreign Application Priority Data

Sep. 11, 1996 [DE] Germany .................. 196 36 880

[51] Int. Cl.[7] .................. C07D 215/20; C09B 25/00
[52] U.S. Cl. .................. 546/154; 8/657; 106/498
[58] Field of Search .................. 546/154; 106/498; 8/657

[56] References Cited

U.S. PATENT DOCUMENTS

| | | | |
|---|---|---|---|
| 3,445,413 | 5/1969 | Jorgensen, Jr. et al. | 260/23 |
| 3,622,583 | 11/1971 | Dehnert | 260/287 R |
| 3,872,131 | 3/1975 | Wallace | 260/289 QP |
| 4,088,651 | 5/1978 | Kalz et al. | 260/287 |
| 4,801,702 | 1/1989 | Bäbler | 540/144 |
| 5,342,950 | 8/1994 | Kilpper et al. | 546/171 |

FOREIGN PATENT DOCUMENTS

| | | |
|---|---|---|
| 1229663 | 6/1967 | Germany . |
| 1184547 | 3/1970 | United Kingdom . |
| 1396766 | 6/1975 | United Kingdom . |

OTHER PUBLICATIONS

Abstract, JP–A–5859971, Week K20, Textiles: Paper: Cellulose p. 3, J5–F (date unavailable).
Abstract, FR 1,403,435, Textiles, Dyeing, Paper, Cellulose, p. 2, French 18.6.65: Indian 19 & 26.6.65, vol. 5, No. 29 (date unavailable).

*Primary Examiner*—Evelyn Mei Huang
*Attorney, Agent, or Firm*—Joseph C. Gil; Richard E. L. Henderson

[57] ABSTRACT

The present invention relates to a process for preparing compounds of formula (I)

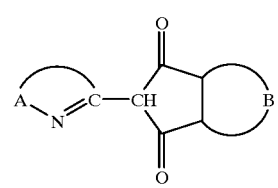

(I)

wherein

A completes an unsubstituted or substituted heteroaromatic ring and

B completes an unsubstituted or substituted aromatic ring, by reacting a heterocyclic compound of formula (II)

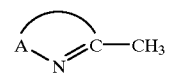

(II)

wherein A completes an unsubstituted or substituted heteroaromatic ring, with an aromatic dicarboxylic acid of formula (III)

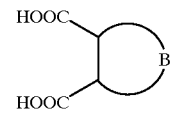

(III)

or an anhydride thereof, wherein B completes an unsubstituted or substituted aromatic ring, in an organic solvent in the presence of an aliphatic or aromatic alcohol that is different from both the organic solvent and compounds (I), (II), and (III).

12 Claims, No Drawings

PROCESS FOR THE PREPARATION OF QUINOPHTHALONES

The present invention relates to a process for the preparation of quinophthalones and to the use of the quinophthalones prepared in this manner for bulk dyeing of plastics.

Quinophthalones of the formula (I)

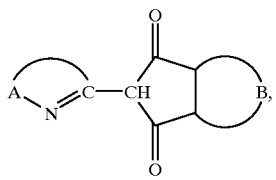

(I)

wherein the grouping A completes an unsubstituted or substituted heteroaromatic ring and the grouping B completes an aromatic ring, which can be unsubstituted or substituted, are already known and are as a rule prepared by reaction of a heterocyclic compound of the general formula (II)

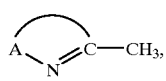

(II)

with an aromatic dicarboxylic acid of the general formula (III)

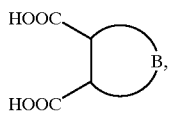

(III)

or anhydrides thereof.

This reaction is carried out, for example, in the melt (DE-A 1 229 663) or in an inert solvent.

The sole use of inert solvents, such as, for example, nitrobenzene, o-dichlorobenzene, trichlorobenzene, dimethylformamide or diphenyl ether, is known, for example, from GB-A 1 225 336 or GB-A 1 199 098 and requires very high temperatures. A disadvantage of this process is the high reaction temperatures, which on the one hand necessitate introduction of large amounts of energy and on the other hand result in corresponding proportions of by-products, so that there is an increased purification requirement on the resulting products. This is accompanied by inadequate space/time yields.

The object of the present invention was to provide a process for the preparation of quinophthalones which no longer has the disadvantages mentioned. A process has now been found for the preparation of quinophthalones of the formula (I) by reaction of compounds of the formula (II) with aromatic dicarboxylic acids of the formula (III) or anhydrides thereof in an organic solvent, which is characterized in that the reaction is carried out in the presence of an aliphatic or aromatic alcohol, this differing both from the solvent used and from the compounds of the formula (I) to (III).

Compounds of the formula (I) which are preferably prepared by the process according to the invention are those which correspond to the formula (Ia)

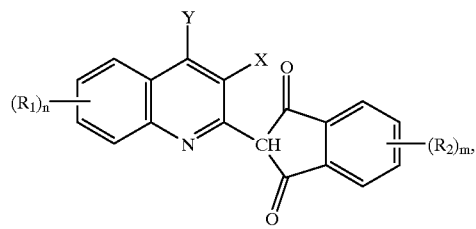

(Ia)

wherein

X represents H or OH,

Y denotes H, halogen, such as Cl, Br and F, $C_1$–$C_4$-alkyl, $C_1$–$C_4$-alkoxy, $C_6$–$C_{10}$-aryl, such as phenyl, or carboxamide, such as $CONH_2$, $R_1$ represents $C_1$–$C_4$-alkyl, $C_1$–$C_4$-alkoxy or halogen, such as Cl, Br and F, n denotes a number from 0 to 4, $R_2$ represents halogen, such as Cl, Br and F, $NO_2$, $NH_2$, NH—($C_1$–$C_4$-alkyl), NH(acyl), OH, $C_1$–$C_4$-alkoxy, $C_1$–$C_4$-alkyl or —O-acyl, such as —O-acetyl and —O-propionyl, and m denotes a number from 0 to 4.

Preferred heterocyclic compounds of the formula (II) are those which correspond to the formula (IIa)

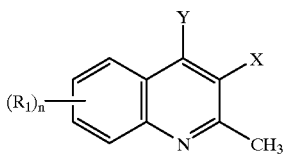

(IIa)

and preferred aromatic dicarboxylic acids of the formula (III) are those which correspond to the formula (IIIa)

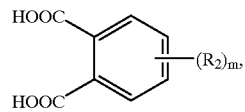

(IIIa)

or anhydrides thereof, wherein X, Y, $R_1$, $R_2$, n and m have the abovementioned meaning.

Preferred compounds of the formula (II) are, for example, 2-methylpyridine, 2-methylbenzimidazole, 2-methylbenzothiazole, 2-methylquinazol-4-one, 8-aminoquinaldine, quinaldine, 3-hydroxyquinaldine, 3-hydroxy-4-carboxy-quinaldines, 3-hydroxy-4-carbomethoxyquinaldine or 3-hydroxy-6-methyl-quinaldine.

Preferred compounds of the formula (IIIa) or anhydrides thereof are, for example, phthalic anhydride, trimellitic anhydride, naphthaline-1,2-dicarboxylic acid anhydride, tetrabromophthalic anhydride, tetrachlorophthalic anhydride, 3- and 4-nitro-phthalic anhydride, 3- and 4-aminophthalic anhydride, 3- and 4-acetyl-aminophthalic anhydride, 4-hydroxyphthalic anhydride and methyl and phenyl trimellitate.

The starting compounds (II) and (III) or (IIa) and (IIIa) are known or are obtainable by known methods.

Preferred quinophthalones of the formula (I) correspond to the formula (Ib)

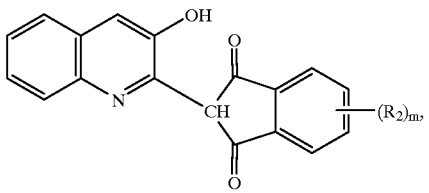

(Ib)

wherein $R_2$ represents halogen, O-acyl, $NH_2$ or NH-acyl, such as NH-acetyl, NH-propionyl and NH-benzoyl, and m represents a number from 0 to 4.

Preferred organic solvents which may be mentioned are nitrobenzene, aromatic chlorohydrocarbons, such as o-dichlorobenzene and trichlorobenzene, dimethylformamide, N-methylpyrrolidone, aromatic ethers and esters, such as dimethyl phthalate, diphenyl ether and ditolyl ether, or a mixture thereof.

Ditolyl ether is particularly preferred as the solvent.

Preferred aliphatic alcohols which may be mentioned, which differ from the solvent used and the compounds (I) to (III), are optionally substituted $C_1–C_{12}$-alcohols, which can be straight-chain or branched. Preferred substituents which may be mentioned are, for example: $C_1–C_4$-alkoxy, $C_1–C_4$-alkoxy-$C_1–C_4$-alkoxy, COOH, OH or phenyl. Particularly preferred possible aliphatic alcohols are, for example: methanol, ethanol, propanol, butanol, dodecyl alcohol, ether-alcohols, such as 2-(2-butoxy-ethoxy)-ethanol, hydroxycarboxylic acids, such as hydroxyacetic acid, DL-lactic acid and DL-malic acid, and araliphatic alcohols, such as benzyl alcohol, or mixtures thereof.

Possible preferred aromatic alcohols which differ from the solvent used and the compounds (I) to (III) are optionally substituted or unsubstituted phenol or naphthols. Preferred substituents which may be mentioned are, for example: $C_1–C_{14}$-alkyl, in particular methyl, ethyl, propyl, tert-butyl, nonyl and dodecyl, $C_1–C_6$-alkoxy, in particular methoxy, $NO_2$, COOH and OH. Particularly preferred aromatic alcohols are: phenol, 2-, 3- and 4-methylphenol, 2-, 3- and 4-propylphenol, 2-, 3- and 4-tert-butylphenol, 2,3-, 3,4-, 2,4-, 3,5-, 2,5- and 2,6-dimethylphenol, nonylphenol, dodecylphenol, α-naphthol, β-naphthol, $C_1–C_6$-alkoxyphenols, such as 4-methoxyphenol, nitrophenol, such as p-nitrophenol, aromatic hydroxycarboxylic acids, such as salicylic acid, 2- 4- and 5-methylsalicylic acid and 5-tert-butylsalicylic acid, salicylic acid alkyl esters, 2-hydroxy-1-naphthalene-carboxylic acid, 1-hydroxy-2-naphthalene-carboxylic acid and 2,4-dihydroxybenzoic acid, or mixtures thereof.

Aromatic alcohols, in particular phenol, salicylic acid, 2-hydroxy-1-naphthalene-carboxylic acid and 1-hydroxy-2-naphthalenecarboxylic acid, are especially preferably used in the process according to the invention.

The proportion of aliphatic and aromatic alcohol used is preferably 0.5 to 2 mol per mole of component of the formula (III).

A molar ratio of compound (II) to (III) which is in general 1:2, in particular 1:1.5 to 1:1.0, preferably 1:1.2 to 1:1.1, is preferred.

The anhydride of the dicarboxylic acid (III) is preferably employed.

As regards process technology, a procedure is in general followed in which components (II) and (III) and the solvent and the aliphatic and/or aromatic alcohol are heated to the reaction temperature, the water of condensation being distilled off.

The process according to the invention is in general carried out at temperatures of 100 to 200° C., preferably at 135 to 200° C., in particular at 160 to 180° C.

The reaction is expediently carried out under normal pressure, but it can also be carried out under 1 to 10 bar, preferably 1 to 5 bar.

If aliphatic or aromatic alcohols which have a boiling point below 160° C. are used, it may be advantageous to carry out the process according to the invention under pressure.

Working up of the reaction mixture to isolate the process products is carried out in a manner known per se, and in particular preferably by dilution with solvents which are water-miscible, such as, for example, methanol and ethanol, at temperatures below 100° C., and subsequent filtration at room temperature or elevated temperature, particularly preferably by direct filtration of the solution at a temperature of 50 to 110° C.

The isolation of the quinophthalones of the formula (I) is preferably carried out in the customary manner by washing the material on the filter with the solvent or water and if appropriate drying it.

The quinophthalones prepared by the process according to the invention are used, for example, as dyestuffs for printing inks and for spin and bulk dyeing of thermoplastics, such as polystyrene, polyvinyl chloride, polyamides, polyesters, polyacrylonitrile, cellulose triacetate and cellulose acetate.

Compared with that of the prior art, the process according to the invention is distinguished by a procedure which is simpler in terms of process technology, a good yield and a high product purity.

Bulk dyeing of plastics here is understood as meaning, in particular, processes in which the dyestuff is incorporated into the molten composition of the plastic, for example with the aid of an extruder, or in which the dyestuff is already added to starting components for the preparation of the plastic, for example monomers before the polymerization.

Particularly preferred plastics are thermoplastics, for example vinyl polymers, polyesters, polyamides or polycarbonates.

Suitable vinyl polymers are polystyrene, styrene/acrylonitrile copolymers, styrene/butadiene copolymers, styrene/butadiene/acrylonitrile terpolymers, polymethacrylate, polyvinyl chloride and others.

Polyesters which are furthermore suitable are: polyethylene terephthalate, polycarbonates and cellulose esters.

Polystyrene, styrene copolymers, polycarbonates and polymethacrylate are preferred. Polystyrene is particularly preferred.

The high molecular weight compounds mentioned can be present individually or in mixtures, as plastic compositions or melts.

The quinophthalones prepared by the process according to the invention are used in finely divided form, it being possible, but not necessary, for dispersing agents to be co-used.

If the compounds of the formula (I) obtained by the process according to the invention are employed after the polymerization, they are preferably mixed or ground with the granules of plastic in the dry state, and this mixture is plasticized and homogenized, for example on mixing rolls or in extruders. However, the dyestuffs can also be added to the molten composition and distributed homogeneously by stirring. The material predyed in this way is then further processed in the customary manner, for example by spinning to bristles, threads and the like or by extrusion or in the injection-moulding process to give mouldings.

The compounds of the formula (I) are preferably employed for dyeing the polymers mentioned in amounts of 0.0001 to 1% by weight, in particular 0.01 to 0.5% by weight, based on the amount of polymer.

Corresponding valuable opaque dyeings can be obtained by addition of pigments which are insoluble in the polymers, such as, for example, titanium dioxide.

Titanium dioxide can be used in an amount of 0.01 to 10% by weight, preferably 0.1 to 5% by weight, based on the amount of polymer.

EXAMPLE 1

13.8 g of salicylic acid (0.1 mol), 25.5 g of hydroxyquinaldinecarboxylic acid (0.126 mol) of the formula

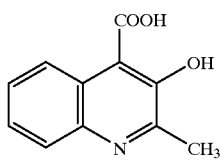

and 29.6 g of phthalic anhydride (0.2 mol) were introduced into 150 ml of ditolyl ether (isomer mixture). The mixture was then heated to 180° C., while passing over nitrogen. Carbon dioxide was split off and water of reaction was distilled off from the condensation reaction. After about 12 hours, the formation of dyestuff had ended. The mixture was cooled to 120° C. and 250 ml of methanol were allowed to run in in order to bring crystallization of the dyestuff to completion. After cooling to room temperature, the dyestuff was filtered off with suction, washed first with 250 ml of methanol and then with 500 ml of hot water and dried in vacuo. Yield: 34 g=93% of theory of the quinophthalone of the formula

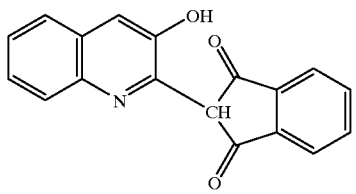

EXAMPLE 2

9.5 g of phenol (0.1 mol), 25.5 g of hydroxyquinaldinecarboxylic acid (0.126 mol) of the formula

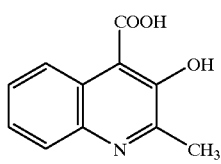

and 29.6 g of phthalic anhydride (0.2 mol) were introduced into 150 ml of ditolyl ether (isomer mixture), while stirring. While passing a stream of nitrogen over the reaction mixture, the reaction mixture was heated to 165° C. and kept at this temperature for 15 hours. When the formation of the dyestuff had ended, the mixture was cooled to 120° C. Thereafter, 250 ml of methanol were added. After cooling to room temperature, the dyestuff which had precipitated out was filtered off with suction and washed with 250 ml of methanol and then with 500 ml of hot water. The dyestuff was then dried in vacuo at 70° C. Yield: 34.4 g=95% of theory of the quinophthalone of the formula

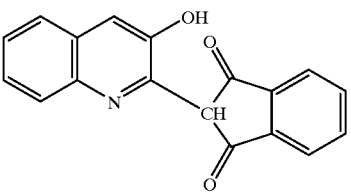

If ditolyl ether was replaced by diphenyl ether or o-dichlorobenzene as the solvent, an equally good result was obtained.

EXAMPLE 3

Comparison

If the procedure was analogous to Example 1, but without the addition of the aromatic alcohol, the yields of the quinophthalone were significantly lower. The following pattern resulted for various solvents.

|  | Yield | |
| --- | --- | --- |
| Solvent | g | % of theory |
| Ditolyl ether | 24 | 66 |
| Dimethyl phthalate | 19.5 | 53.7 |
| N-methylpyrrolidone | 19.9 | 54.8 |

EXAMPLE 4

150 ml of ditolyl ether (isomer mixture) were mixed with 26.2 g of dodecylphenol (0.1 mol), 25.5 g (0.126 mol) of hydroxyquinaldinecarboxylic acid and 29.6 g (0.2 mol) of phthalic anhydride, while stirring, and the mixture was heated at 180° C. under nitrogen. During this procedure, water of reaction was distilled off. The temperature was maintained for 15 hours. Thereafter, the mixture was cooled to 120° C. and 250 ml of methanol were added. After cooling to room temperature, the quinophthalone dyestuff which had crystallized out was filtered off, washed with 250 ml of methanol and then washed with 500 ml of hot water. The product was dried at 70° C. in vacuo. Yield: 33.1 g=90.5% of theory.

EXAMPLE 5

150 ml of ditolyl ether (isomer mixture), 15 g of 4-tert-butylphenol (0.1 mol), 25.5 g of hydroxyquinaldinecarboxylic acid (0.126 mol) and 29.6 g of phthalic anhydride, (0.2 mol) were heated to 175° C., while stirring, a stream of nitrogen being passed over and water of reaction being distilled off. After a reaction time of 15 hours, the formation of the dyestuff had ended. The reaction mixture was cooled to 120° C. and 250 ml of methanol were added. The mixture was stirred at 65 to 68° C. for a further hour and then allowed to cool to room temperature. The quinophthalone dyestuff which had crystallized out was filtered off with suction and washed with 250 ml of methanol. Thereafter, the dyestuff was washed with 500 ml of hot water and dried at 70° C. in vacuo. Yield: 33.3 g=91.1% of theory.

EXAMPLE 6

150 ml of ditolyl ether (isomer mixture), 18.8 g of 2-naphthol-1-carboxylic acid (0.1 mol), 25.5 g of hydroxyquinaldinecarboxylic acid (0.126 mol) and 29.6 g of phthalic anhydride (0.2 mol) were heated to 200° C., while stirring and passing over nitrogen. During this procedure, water of reaction was distilled off. After a reaction time of 10 hours, the entire starting material had been converted into the quinophthalone dyestuff The mixture was cooled to 120° C., 250 ml of methanol were added and the mixture was allowed to cool to room temperature. The dyestuff was then filtered off, washed first with 250 ml of methanol and then with 500 ml of hot water and dried in vacuo at 70° C. Yield: 33.5 g=91.6% of theory.

EXAMPLE 7

150 ml of diphenyl ether, 11.7 g of hydroxyacetic acid (0.15 mol), 25.5 g of hydroxyquinaldinecarboxylic acid (0.126 mol) and 29.6 g of phthalic anhydride (0.2 mol) were heated to 180° C., while stirring. During this procedure, a stream of nitrogen was passed over and water of reaction was distilled off. After 10 hours, the reaction had ended. The mixture was cooled to 120° C. and diluted with 250 ml of methanol. Thereafter, it was allowed to cool to room temperature and the quinophthalone dyestuff which had crystallized out was filtered off. The product was washed with 250 ml of methanol and then with 500 ml of hot water and dried at 70° C. in vacuo. Yield: 32.9 g=90.5% of theory.

EXAMPLE 8

150 ml of ditolyl ether (isomer mixture), 13.8 g of salicylic acid (0.1 mol), 25.5 g of hydroxyquinaldinecarboxylic acid (0.126 mol) and 40.0 g of tetrachlorophthalic anhydride (0.14 mol) were heated to 170° C., while stirring and passing over nitrogen. During this procedure, water of reaction was distilled off. After a reaction time of 12 hours, the reaction mixture was cooled to 120° C. and diluted with 250 ml of methanol. The quinophthalone dyestuff crystallized out during this procedure and was isolated by filtration. The filter cake was washed with 250 ml of methanol and then with 500 ml of hot water and was subsequently dried in vacuo at 70° C. The dyestuff has the structural formula

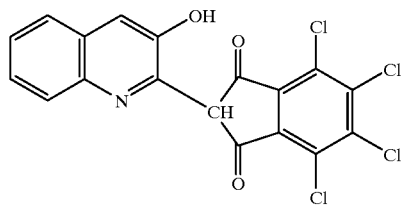

Yield: 39.7 g=93% of theory.

EXAMPLE 9

150 ml of ditolyl ether (isomer mixture), 8.8 g of isopentyl alcohol (0.1 mol), 25.5 g of hydroxyquinaldinecarboxylic acid (0.126 mol) and 27.4 g of 4-chloro-phthalic anhydride were heated to 160° C., while stirring and passing over nitrogen. During this procedure, water of reaction was distilled off. After a reaction time of 12 hours, the reaction mixture was cooled to 120° C. and 250 ml of methanol were added. The quinophthalone dyestuff crystallized out and was filtered off. The filter cake was washed with 250 ml of methanol and then with 500 ml of hot water and finally dried in vacuo at 70° C. The dyestuff has the structural formula

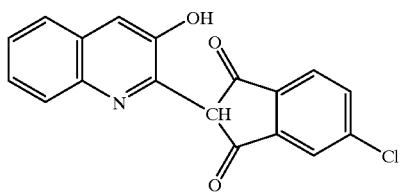

Yield: 37 g=91% of theory.

What is claimed is:

1. A process for the preparation of a quinophthalone compound of formula (I)

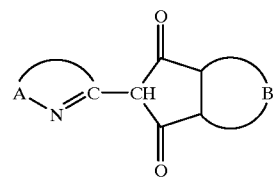

wherein

A completes an unsubstituted or substituted heteroaromatic ring and

B completes an unsubstituted or substituted aromatic ring, comprising reacting a heterocyclic compound of formula (II)

(II)

$$A\underset{N}{\diagup}C-CH_3$$

wherein A completes an unsubstituted or substituted heteroaromatic ring, with an aromatic dicarboxylic acid of formula (III)

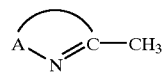

or an anhydride thereof, wherein B completes an unsubstituted or substituted aromatic ring, in an organic solvent in the presence of 0.5 to 2 mol, per mol of the aromatic dicarboxylic acid, of a substituted or unsubstituted phenol or naphthol or mixture thereof that is different from both the organic solvent and the compounds of formulas (I), (II), and (III).

2. The process according to claim 1 wherein the compound prepared thereby is a compound of formula (Ia)

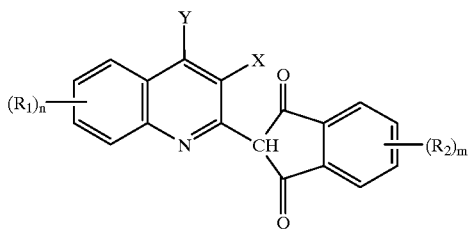

wherein

X represents H or OH,

Y represents H, halogen, $C_1-C_4$-alkyl, $C_1-C_4$-alkoxy, $C_6-C_{10}$-aryl, or carboxamide, $R_1$ represents $C_1-C_4$-alkyl, $C_1-C_4$-alkoxy, or halogen, n denotes a number from 0 to 4

$R_2$ represents halogen, $NO_2$, $NH_2$, $NH(C_1-C_4$-alkyl), NH(acyl), OH, $C_1-C_4$-alkoxy, $C_1-C_4$-alkyl, or O-acyl, and m denotes a number from 0 to 4.

3. The process according to claim 1 wherein the compound prepared thereby is a compound of formula (Ia)

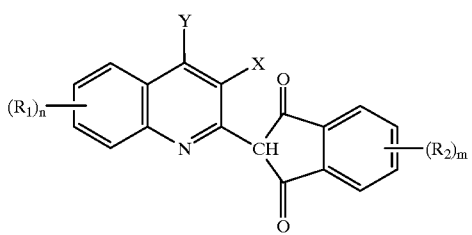

wherein

X represents H or OH,

Y represents H, Cl, Br, F, $C_1-C_4$-alkyl, $C_1-C_4$-alkoxy, phenyl, or $CONH_2$, $R_1$ represents $C_1-C_4$-alkyl, $C_1-C_4$-alkoxy, Cl, Br, or F, n denotes a number from 0 to 4, $R_2$ represents Cl, Br, F, $NO_2$, $NH_2$, $NH(C_1-C_4$-alkyl), NH(acyl), OH, $C_1-C_4$-alkoxy, $C_1-C_4$-alkyl, O-acetyl, or O-propionyl, and m denotes a number from 0 to 4.

4. The process according to claim 1 wherein the heterocyclic compound is a compound of formula (IIa)

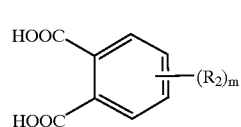

wherein

X represents H or OH,

Y represents H, halogen, $C_1-C_4$-alkyl, $C_1-C_4$-alkoxy, $C_6-C_{10}$-aryl, or carboxamide, $R_1$ represents $C_1-C_4$-alkyl, $C_1-C_4$-alkoxy, or halogen, and n denotes a number from 0 to 4, and the aromatic dicarboxylic acid or anhydride thereof is a compound of formula (IIIa)

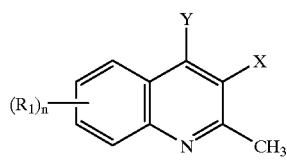

or an anhydride thereof, wherein $R_2$ represents halogen, $NO_2$, $NH_2$, $NH(C_1-C_4$-alkyl), NH(acyl), OH, $C_1-C_4$-alkoxy, $C_1-C_4$-alkyl, or O-acyl, and m denotes a number from 0 to 4.

5. The process according to claim 1 wherein the heterocyclic compound is a compound of formula (IIa)

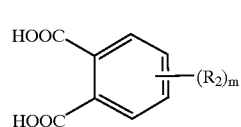

wherein

X represents H or OH,

Y represents H, Cl, Br, F, $C_1-C_4$-alkyl, $C_1-C_4$-alkoxy, phenyl, or $CONH_2$, $R_1$ represents $C_1-C_4$-alkyl, $C_1-C_4$-alkoxy, Cl, Br, or F, and n denotes a number from 0 to 4, and the aromatic dicarboxylic acid or anhydride thereof is a compound of formula (IIIa)

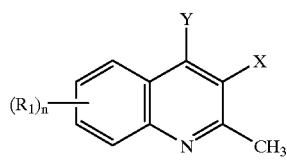

or an anhydride thereof, wherein $R_2$ represents Cl, Br, F, $NO_2$, $NH_2$, $NH(C_1-C_4$-alkyl), NH(acyl), OH, $C_1-C_4$-alkoxy, $C_1-C_4$-alkyl, O-acetyl, or O-propionyl, and m denotes a number from 0 to 4.

6. The process according to claim 1 wherein the compound of formula (II) is 2-methylpyridine, 2-methylbenzimidazole, 2-methylbenzothiazole, 2-methylquinazol-4-one, 8-aminoquinaldine, quinaldine, 3-hydroxyquinaldine, 3-hydroxy-4-carboxyquinaldine, 3-hydroxy-4-carbomethoxyquinaldine, or 3-hydroxy-6-methylquinaldine.

7. The process according to claim 1 wherein the compound of formula (III) is phthalic anhydride, trimellitic anhydride, naphthalene-1,2-dicarboxylic acid anhydride, tetrabromophthalic anhydride, tetrachlorophthalic anhydride, 3- or 4-nitrophthalic anhydride, 3- or 4-amino-4-hydroxyphthalic anhydride, or methyl or phenyl trimellitate.

8. The process according to claim 1 wherein the compound prepared thereby is a compound of formula (Ib)

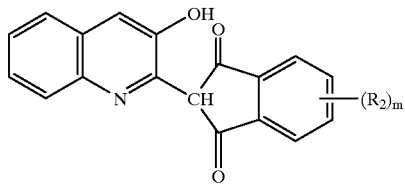

wherein $R_2$ represents halogen, O-acyl, $NH_2$, or NH(acyl), and m denotes a number from 0 to 4.

9. The process according to claim 1 wherein the compound prepared thereby is a compound of formula (Ib)

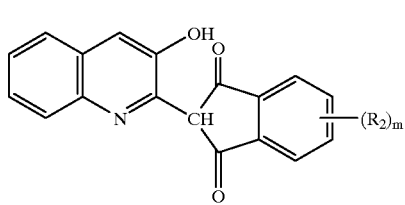

wherein $R_2$ represents halogen, O-acyl, $NH_2$, NH-acetyl, NH-propionyl, or NH-benzoyl, and m denotes a number from 0 to 4.

10. The process according to claim 1 wherein the organic solvent is nitrobenzene, an aromatic chlorohydrocarbon, dimethylformamide, N-methylpyrrolidone, an aromatic ether, an aromatic ester, or a mixture thereof.

11. The process according to claim 1 wherein the phenol or naphthol is phenol, 2-, 3-, or 4-methylphenol, 2-, 3-, or 4-propylphenol, 2-, 3-, or 4-tert-butylphenol, 2,3-, 3,4-, 2,4-, 3,5-, 2,5-, or 2,6-dimethylphenol, nonylphenol, dodecylphenol, α-naphthol, β-naphthol, a $C_1$–$C_6$-alkoxyphenol, nitrophenol, an aromatic hydroxycarboxylic acid or alkyl ester thereof, or mixtures thereof.

12. The process according to claim 1 wherein the phenol or naphthol is phenol, 2-, 3-, or 4-methylphenol, 2-, 3-, or 4-propylphenol, 2-, 3-, or 4-tert-butylphenol, 2,3-, 3,4-, 2,4-, 3,5-, 2,5-, or 2,6-dimethylphenol, nonylphenol, dodecylphenol, α-naphthol, β-naphthol, 4-methoxyphenol, p-nitrophenol, salicylic acid, 2-, 4-, or 5-methylsalicylic acid, 5-tert-butylsalicylic acid, a salicylic acid alkyl ester, 2-hydroxy-1-naphthalenecarboxylic acid, 1-hydroxy-2-naphthalenecarboxylic acid, 2,4-hydroxybenzoic acid, or mixtures thereof.

* * * * *